United States Patent [19]

Shirota

[11] Patent Number: 4,534,150
[45] Date of Patent: Aug. 13, 1985

[54] TOOL FOR USE WITH REFILLING EMPTY AMPULES WITH DENTAL IMPRESSION MATERIALS

[75] Inventor: Kazunori Shirota, Tokyo, Japan

[73] Assignee: Shirota Denki Rozai Kabushiki Kaisha, Tokyo, Japan

[21] Appl. No.: 456,374

[22] Filed: Jan. 7, 1983

[51] Int. Cl.³ .............................................. B65B 67/00
[52] U.S. Cl. ..................................... 53/390; 141/205; 604/411
[58] Field of Search ................ 604/411, 414; 141/285, 141/329, 330, 19; 269/54.5; 53/390, 235

[56] References Cited

U.S. PATENT DOCUMENTS 3,731,453  5/1973  Porteous ............................. 53/471

Primary Examiner—E. Michael Combs
Attorney, Agent, or Firm—Shlesinger Fitzsimmons Shlesinger

[57] ABSTRACT

A block-like tool has a hole in its upper surface and contains a hollow needle projecting at one of its ends into said hole and opening at its other end to the atmosphere. Said hole is disposed removably to receive and stably support therein the lower end of an empty, tubular ampule, which is hermetically sealed at its lower end by an elastic diaphragm. Said needle pierces said diaphragm when the ampule is mounted on the tool, whereby the interior of the ampule is also brought to atmospheric pressure through said needle thus enabling the withdrawal of an elastic plug from the ampule, and the refilling of the ampule with a solid alginate without encountering pneumatic resistance.

4 Claims, 16 Drawing Figures

U.S. Patent  Aug. 13, 1985  Sheet 1 of 4  4,534,150
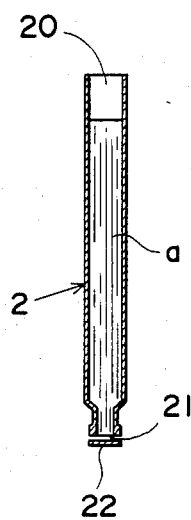
FIG 1
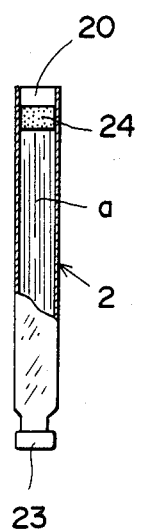
FIG 2
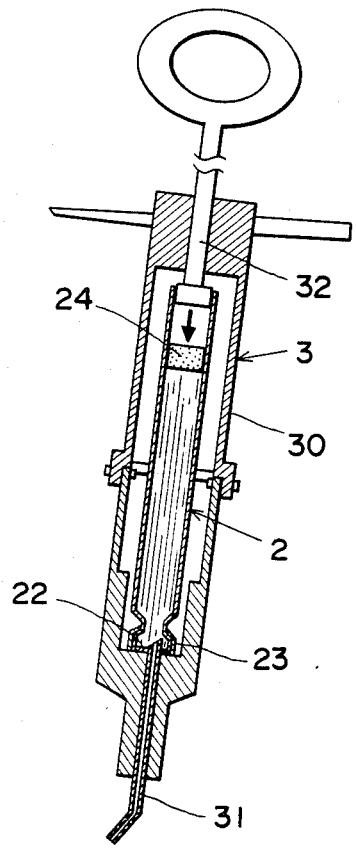
FIG 3
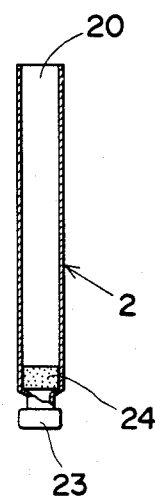
FIG 4
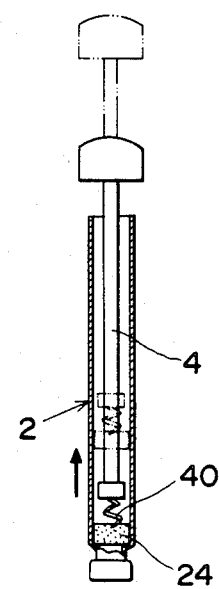
FIG 5
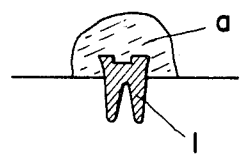

1

TOOL FOR USE WITH REFILLING EMPTY AMPULES WITH DENTAL IMPRESSION MATERIALS

BACKGROUND OF THE INVENTION

This invention relates to a tool utilized for refilling a used, empty ampule of a dental impression material injection syringe with impression materials such as alginate.

Such ampule used with the syringe for injecting dental alginate impression materials is first explained with reference to the accompanying drawing. As illustrated in FIG. 3, an impression of a treated tooth 1 is taken by injecting an impression material a over said tooth, and according to which impression a crown to be covered over the tooth is made by casting. Said impression material a such as alginate is hermetically contained in an ampule 2 such as illustrated in FIG. 2. The ampule commonly made from glass, is a tube having an upper opening 20 and a lower neck opening 21. In a factory, the impression material is warmed and made liquid, and then charged into the tube. When it is solidified, the lower neck opening 21 of the tube is sealed by a rubber diaphragm 22 which is in turn fastened by a metal ring cap 23. A rubber plug 24 is insertedly fitted to the upper opening 20.

This tubular ampule is mounted by a dentist on the injection syringe 3, cylinder 30 of which is open at its side, whereby an injection needle 31 pierces through the rubber diaphragm 22 of ampule 2, and a piston 32 engages to the upper opening 20 of the ampule. The injection syringe 3 with the ampule 2 is warmed so as to make the impression material a softened. Then, the piston 32 is pressed downwardly, resulting in having the rubber plug 24 descended and consequently resulting in having the alginate a injected through the needle 31.

The ampule thus used and made empty has seldom been reused by a dentist, because of the following reasons.

It is nearly impossible to take out from the ampule the rubber plug 24 which has been pushed down to the bottom of the ampule (FIG. 4). Even a tool 40 such as shown in FIG. 5 which is engageable with the plug 24 by its screwed hook 40, can not successfully draw out the plug, mainly on account of a large negative pressure existing below the plug. And, even if the rubber plug 24 were to be successfully drawn out, a stick-like solid alginate can not be inserted into the ampule against air existing thereing. It shall be an idea to make the alginate liquid and pour it into the ampule, but this requires specific installations. It shall be another idea to tear down the metal ring cap 23 and refasten the lower neck opening 21 with a new cap again after the ampule has been refilled with alginate. But, this requires also specific devices.

In view of the above, this invention is to provide a simple tool which is advantageously utilized by a dentist on a small scale as he requires for manually refilling an empty ampule with dental impression materials such as alginate.

BRIEF DESCRIPTION OF THE DRAWING

FIG. 1 is a vertical sectional side view of a glass tube in order to explain how the tube is charged with dental impression materials in a factory, FIG. 2 is a side view partly in section of the glass ampule tube charged with the impression materials and hermetically sealed, FIG. 3 is a vertical sectional side view of the ampule mounted to an injecton syringe, FIG. 4 is a side view partly in section of the ampule from which the impression materials have been discharged, FIG. 5 is a view for explaining a step for taking out a rubber plug from the used empty ampule.

DETAILED DESCRIPTION OF THE INVENTION

Figure 6:
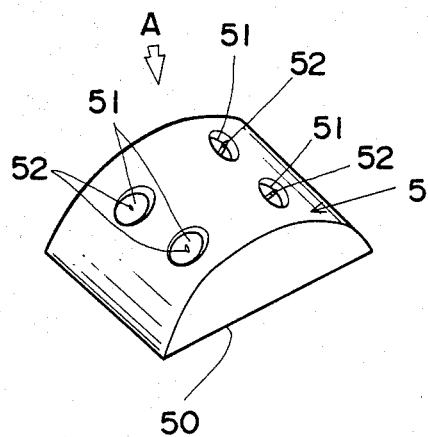
FIG. 6 is a perspective view of a tool made in accordance with this invention.
Figure 7:
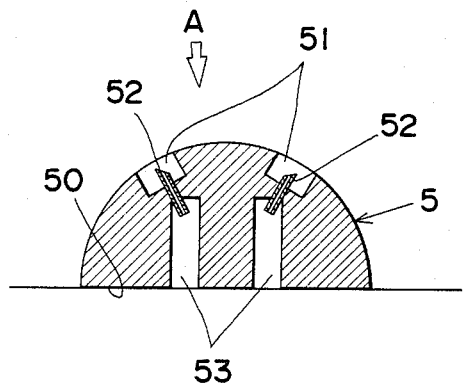
FIG. 7 is a side sectional view of said tool.

The tool A made in accordance with this invention comprises, as best shown in FIGS. 6 and 7, a base block 5 made from a heavy material such as gunmetal.

The block has a flat bottom 50 so as to be placed on a table, and has in its upper surface four holes 51, diameters and depths of which are such that the lower neck opening 21 sealed by the rubber diaphragm 22 and metal ring cap 23 of the ampule 2 is insertedly supported by each hole 51. A hollow needle 52 with a through hole is provided in each hole 51 so as to project at one end in the hole coaxially therewith for penetrating the rubber diaphragm of the ampule 2, the lower neck opening of which is insertedly supported by the hole 51. The other end of said needle opens to the atmosphere or air.

Figure 11:
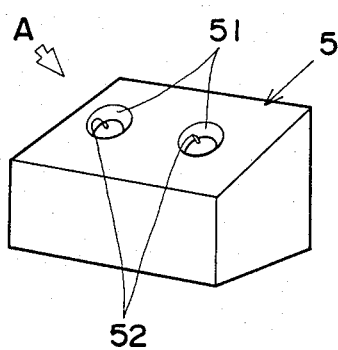
FIG. 11 is a perspective view of another embodiment of the tool made in accordance withe this invention.
Figure 12:
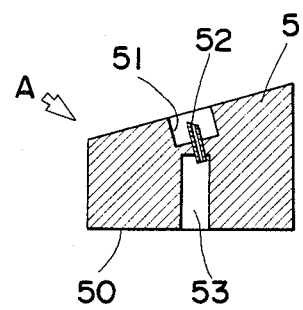
FIG. 12 is a side sectional view of said tool illustrated in FIG. 11.
Figure 13:
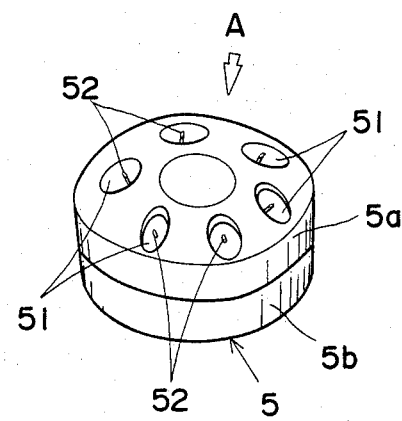
FIG. 13 is a further another embodiment of the tool.
Figure 14:
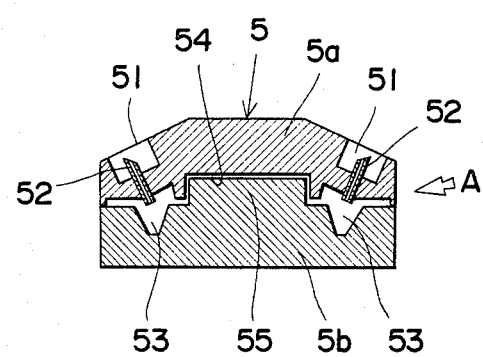
FIG. 14 is a side sectional view of said tool illustrated in FIG. 13.
Figure 15:
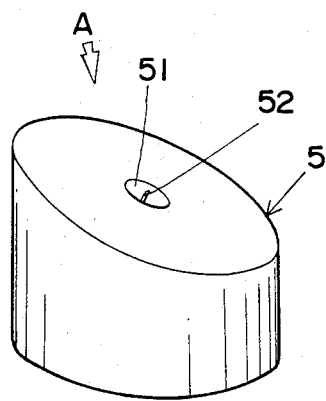
FIG. 15 is a still further another embodiment of the tool.

In this invention, the base block can be of any desired shape. It may be, as illustrated in FIGS. 6 and 7, semicircular in its cross-section, or its cross-section may be, as illustrated in FIGS. 11 and 12, trapezoid. Or, it may be, as illustrated in FIGS. 13 and 14, a disc, or, as illustrated in FIGS. 15 and 16, slanted frusto-cylindrical.

Figure 16:
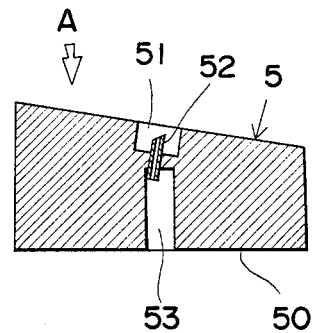
FIG. 16 is a side sectional view of said tool illustrated in FIG. 15.

The communication of the lower end of hollow needle 52 with the air can be made through a cavity 53, the upper closed end of which is located just below the hole 51 and the lower end of which opens at the bottom 50 of block 5, as illustrated in FIGS. 7, 12, and 16. Or, as illustrated in FIGS. 13 and 14 in which the block 5 is divided to an upper half 5a and a lower half 5b, the said communication is established through a circular cavity 53 which horizontally runs at abutting surfaces of said upper and lower halves 5a, 5b, and opens to the air. In this embodiment, the upper half 5a of block is rotatable about a boss 55 which projects centrally from the lower half 5b and rotatably engages with a central circular recess 54 of the upper half block 5a, whereby a series of holes 51 can be utilized in sequence.

The tool made in accordance with this invention, viz., the base block is utlilized for refilling alginate a, in particular of a solid stick form, into the empty glass tube 2, as follows.

Figure 8:
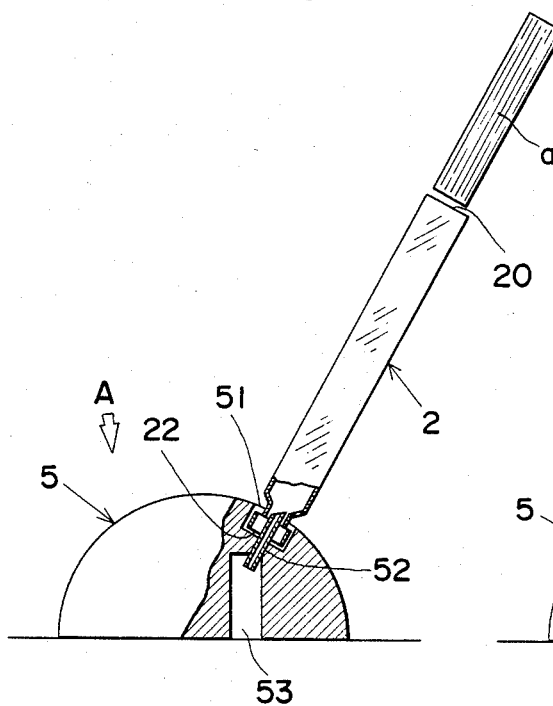
FIGS. 8 and 9 are explanatory views illustrating how to use the tool.

First, the rubber plug 24 which has been pushed deeply to the bottom of ampule 2 which has been used, has to be taken out (FIG. 4). In order to achieve this, the ampule is inserted at its end into the hole 51 (FIG. 8) so that the hollow needle pierces the rubber diaphragm 22. Then, the rubber plug 24 is drawn out from the upper opening 20 of ampule by means of the tool 4 for example. This drawing out is easily accomplished in this invention, because the introduction of air into the ampule below the rubber plug through the needle in consequence with the drawing out of the rubber plug eliminates the negative pressure exerting otherwise below the said plug.

Figure 9:
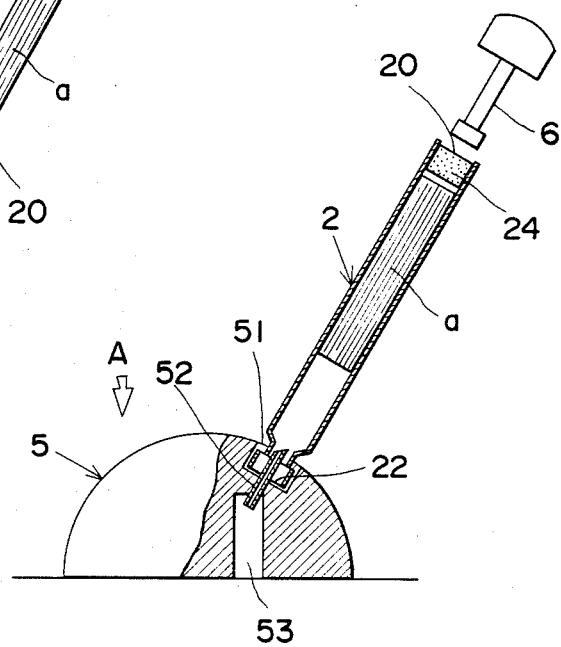
Figure 10:
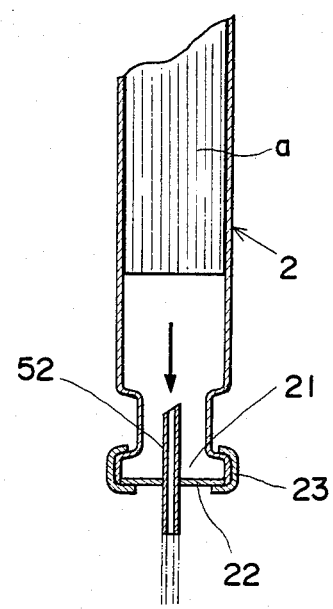
FIG. 10 is an explanatory view showing the operational function of the present tool.

Second, into the glass tube, rubber plug 24 of which has now been removed, the impression material a formed to a solid stick shape, outer diameter of which corresponds to the inner diameter of the glass tube 2 is manually pushed through the upper opening 20. This manual insertion of the stick into the tube 2 utilizing the block tool 5 in accordance with this invention is very smooth, since air within the tube escapes outside through the hollow needle 52 of block 5 in consequence with the said insertion of stick a (FIG. 10). In this instance, no specific pneumatic resistance occurs against the stick alginate. When the stick a is inserted into the tube 2 to an appropriate depth thereof, the rubber plug 24 is placed on the top of the stick alginate. They are further pushed into the tube by a pusher 6 (FIG. 9).

As above-explained, the block tool 5 can achieve the refilling of empty ampules with alginate readily and smoothly. In addition to the various advantages afforded to this invention as mentioned above, it shall be noted that the refilling is made steadily as the ampule is kept stable on the block tool.

It shall be noted also that as the hole extends at a right angle to the curved or slanted upper surface of block 5, the tubular ampules supported by the hole can project radially outwardly above the base block, allowing the ampules to be handled and reached easily.

I claim:

1. A tool for use in refilling dental impression materials into a tubular ampule which has a lower end thereof hermetically sealed by a diaphragm made from elastic materials, said tool comprising a heavy base block having a flat bottom, an upper surface of the block being provided with at least one hole, the diameter and depth of which are such that said hole can stably support therein said lower end of a tubular ampule, and a hollow needle located in said hole with its upper end projecting into the hole coaxially thereof and positioned to have said upper end pierce the elastic diaphragm of said ampule when said lower end thereof is mounted in the hole in said block, a lower end of said needle opening to the air.

2. A tool as claimed in claim 1, in which the base block is made of a single body, and the lower end of said hollow needle is open to the air through a cavity which is provided in the block below said hole and which opens to the air at its bottom, and top of which cavity communicates with said lower end of said needle.

3. A tool as claimed in claim 1, in which the base block comprises an upper block part and a lower block part, said upper block part containing said hole and said needle and being rotatably supported on the said lower block part, and the needle of the upper block part being open to the air through a cavity provided in one of the upper and lower block parts, respectively, at abutting surfaces thereof.

4. A tool as claimed in any one of claims 1 to 3, in which the upper surface of the block is inclined to the bottom thereof, and the axis of said hole extends at a right angle to said inclined surface so that the tubular ampule supported by the hole projects transversely outwardly from said inclined surface above the base block.

* * * * *